US011583349B2

(12) United States Patent
Azizian et al.

(10) Patent No.: US 11,583,349 B2
(45) Date of Patent: Feb. 21, 2023

(54) SYSTEMS AND METHODS FOR PROJECTING AN ENDOSCOPIC IMAGE TO A THREE-DIMENSIONAL VOLUME

(71) Applicant: INTUITIVE SURGICAL OPERATIONS, INC., Sunnyvale, CA (US)

(72) Inventors: Mahdi Azizian, Santa Clara, CA (US); Simon P. DiMaio, San Carlos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 421 days.

(21) Appl. No.: 16/626,001

(22) PCT Filed: Jun. 27, 2018

(86) PCT No.: PCT/US2018/039856
§ 371 (c)(1),
(2) Date: Dec. 23, 2019

(87) PCT Pub. No.: WO2019/006028
PCT Pub. Date: Jan. 3, 2019

(65) Prior Publication Data
US 2020/0253673 A1 Aug. 13, 2020

Related U.S. Application Data
(60) Provisional application No. 62/526,103, filed on Jun. 28, 2017.

(51) Int. Cl.
*A61B 34/35* (2016.01)
*A61B 34/10* (2016.01)
(Continued)

(52) U.S. Cl.
CPC ........ *A61B 34/30* (2016.02); *A61B 1/000094* (2022.02); *A61B 1/00194* (2022.02);
(Continued)

(58) Field of Classification Search
CPC ............... G06T 19/00; G06T 2219/028; G06T 2210/41; A61B 34/20; A61B 34/37;
(Continued)

(56) References Cited

U.S. PATENT DOCUMENTS 8,108,072 B2    1/2012    Zhao et al.
9,101,397 B2    8/2015    Guthart et al.
(Continued)

FOREIGN PATENT DOCUMENTS

EP            2942029 A1    11/2015
WO    WO-2006124388 A1    11/2006
(Continued)

OTHER PUBLICATIONS

International Search Report and Written Opinion for Application No. PCT/US2018/039856, dated Oct. 30, 2018, 7 pages.
(Continued)

*Primary Examiner* — Brenda C Bernardi
(74) *Attorney, Agent, or Firm* — Haynes and Boone, LLP

(57) ABSTRACT

A method comprises obtaining an endoscopic image dataset of a patient anatomy from an endoscopic imaging system and retrieving an anatomic model dataset of the patient anatomy obtained by an anatomic imaging system. The method also comprises mapping the endoscopic image dataset to the anatomic model dataset and displaying a first vantage point image using the mapped endoscopic image dataset. The first vantage point image is presented from a first vantage point at a distal end of the endoscopic imaging system. The method also comprises displaying a second vantage point image using at least a portion of the mapped
(Continued)

endoscopic image dataset. The second vantage point image is presented from a second vantage point, different from the first vantage point.

20 Claims, 7 Drawing Sheets

(51) Int. Cl.
A61B 34/30 (2016.01)
A61B 90/00 (2016.01)
A61B 1/00 (2006.01)

(52) U.S. Cl.
CPC ........ *A61B 34/35* (2016.02); *A61B 2034/105* (2016.02); *A61B 2034/301* (2016.02); *A61B 2090/3762* (2016.02)

(58) Field of Classification Search
CPC . A61B 1/00194; A61B 34/30; A61B 1/00193; A61B 1/000094; A61B 1/313; A61B 34/35; A61B 34/10; A61B 90/36; A61B 2090/364; A61B 2034/301; A61B 2090/3762; A61B 2090/374; A61B 2090/373; A61B 1/00009; A61B 2034/105; A61B 2034/2065; A61B 2576/00; A61B 1/00149
See application file for complete search history.

(56) References Cited

U.S. PATENT DOCUMENTS

| | | | |
|---|---|---|---|
| 9,646,423 B1 | 5/2017 | Sun et al. | |
| 10,064,682 B2 | 9/2018 | Azizian et al. | |
| 10,376,321 B2 | 8/2019 | DiMaio et al. | |
| 2005/0182319 A1 | 8/2005 | Glossop | |
| 2006/0258938 A1 | 11/2006 | Hoffman et al. | |
| 2006/0281971 A1 | 12/2006 | Sauer et al. | |
| 2014/0275760 A1 | 9/2014 | Lee et al. | |
| 2014/0343571 A1 | 11/2014 | Popovic et al. | |
| 2016/0101263 A1* | 4/2016 | Blumenkranz | A61B 5/6852 600/117 |
| 2016/0175057 A1* | 6/2016 | Ibach | A61B 1/00045 600/103 |
| 2017/0079730 A1 | 3/2017 | Azizian et al. | |
| 2017/0172662 A1 | 6/2017 | Panescu et al. | |
| 2017/0181798 A1* | 6/2017 | Panescu | A61B 1/00006 |
| 2018/0021102 A1 | 1/2018 | Azizian et al. | |
| 2018/0228343 A1* | 8/2018 | Seeber | A61B 1/00004 |
| 2020/0093544 A1 | 3/2020 | Azizian | |

FOREIGN PATENT DOCUMENTS

| | | |
|---|---|---|
| WO | WO-2014028394 A1 | 2/2014 |
| WO | WO-2015142798 A1 | 9/2015 |
| WO | WO-2015149043 A1 | 10/2015 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18825307.4 dated Mar. 9, 2021, 07 pages.

* cited by examiner

SYSTEMS AND METHODS FOR PROJECTING AN ENDOSCOPIC IMAGE TO A THREE-DIMENSIONAL VOLUME

CROSS-REFERENCE TO RELATED APPLICATIONS

This application the U.S. national phase of International Application No. PCT/US2018/039856 filed Jun. 27, 2018 which the benefit of U.S. Provisional Application No. 62/526,103, filed Jun. 28, 2017, all of which are incorporated by reference herein in their entirety.

FIELD

The present disclosure is directed to systems and methods for performing a teleoperational medical procedure and more particularly to systems and methods for projecting an endoscopic image to a registered three dimensional volume.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. During procedures in which a real-time surgical environment view is provided by an endoscopic instrument, the surgeon may have limited situational awareness of the environment beyond the vantage point of the endoscopic view. Systems and methods are needs to provide the surgeon with enhanced perspective of the surgical environment beyond the endoscopic view.

SUMMARY

The embodiments of the invention are summarized by the claims that follow below.

In one embodiment, a method comprises obtaining an endoscopic image dataset of a patient anatomy from an endoscopic imaging system and retrieving an anatomic model dataset of the patient anatomy obtained by an anatomic imaging system. The method also comprises mapping the endoscopic image dataset to the anatomic model dataset and displaying a first vantage point image using the mapped endoscopic image dataset. The first vantage point image is presented from a first vantage point at a distal end of the endoscopic imaging system. The method also comprises displaying a second vantage point image using at least a portion of the mapped endoscopic image dataset. The second vantage point image is presented from a second vantage point, different from the first vantage point.

In another embodiment, a system comprises a teleoperational assembly including a plurality of manipulators. A first manipulator of the plurality of manipulators is configured to control movement of an endoscopic imaging system. The system also comprises a processing unit including one or more processors. The processing unit is configured to obtain an endoscopic image dataset of a patient anatomy from an endoscopic imaging system and retrieve an anatomic model dataset of the patient anatomy obtained by an anatomic imaging system. The processing unit is also configured to map the endoscopic image dataset to the anatomic model dataset and display a first vantage point image using the mapped endoscopic image dataset. The first vantage point image is presented from a first vantage point at a distal end of the endoscopic imaging system. The processing unit is also configured to display a second vantage point image using at least a portion of the mapped endoscopic image dataset. The second vantage point image is presented from a second vantage point, different from the first vantage point.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
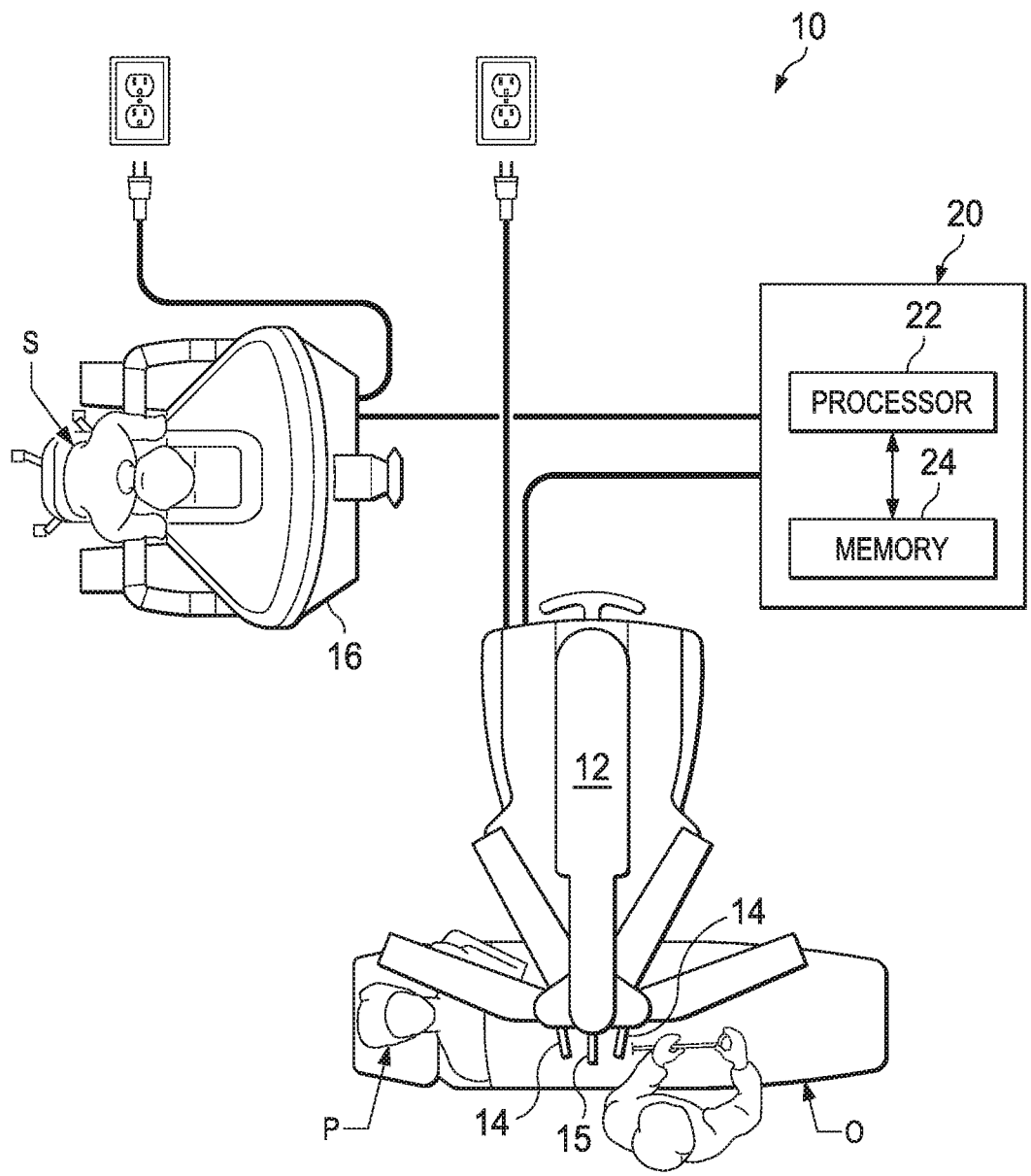
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, touchless hand gesture tracking, eye gaze tracking, electromyography (EMG) sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaw end effectors, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperational assembly 12 to orient the endoscope 15. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Instruments 14 may include end effectors having a single working member such as a scalpel, a blunt blade, an optical fiber, or an electrode. Other end effectors may include, for example, forceps, graspers, scissors, or clip appliers.

The teleoperational medical system 10 also includes a control system 20. The control system 20 includes at least one memory 24 and at least one processor 22, and typically a plurality of processors, for effecting control between the medical instrument system 14, the operator input system 16, and other auxiliary systems 26 which may include, for example, imaging systems, audio systems, fluid delivery systems, display systems, illumination systems, steering control systems, irrigation systems, and/or suction systems. The control system 20 can be used to process the images of the surgical environment from the imaging system 15 for subsequent display to the surgeon S through the surgeon's console 16. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The control system 20 can be coupled with the endoscope 15 and can include a processor to process captured images for subsequent display, such as to a surgeon on the surgeon's console, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

In alternative embodiments, the teleoperational system may include more than one teleoperational assembly and/or more than one operator input system. The exact number of manipulator assemblies will depend on the surgical procedure and the space constraints within the operating room, among other factors. The operator input systems may be co-located, or they may be positioned in separate locations. Multiple operator input systems allow more than one operator to control one or more manipulator assemblies in various combinations. Multiple operator input systems also allow one or more operators to function as mentors for one or more other operators by demonstrating control of one or more manipulator assemblies for the mentees.

Figure 1B:
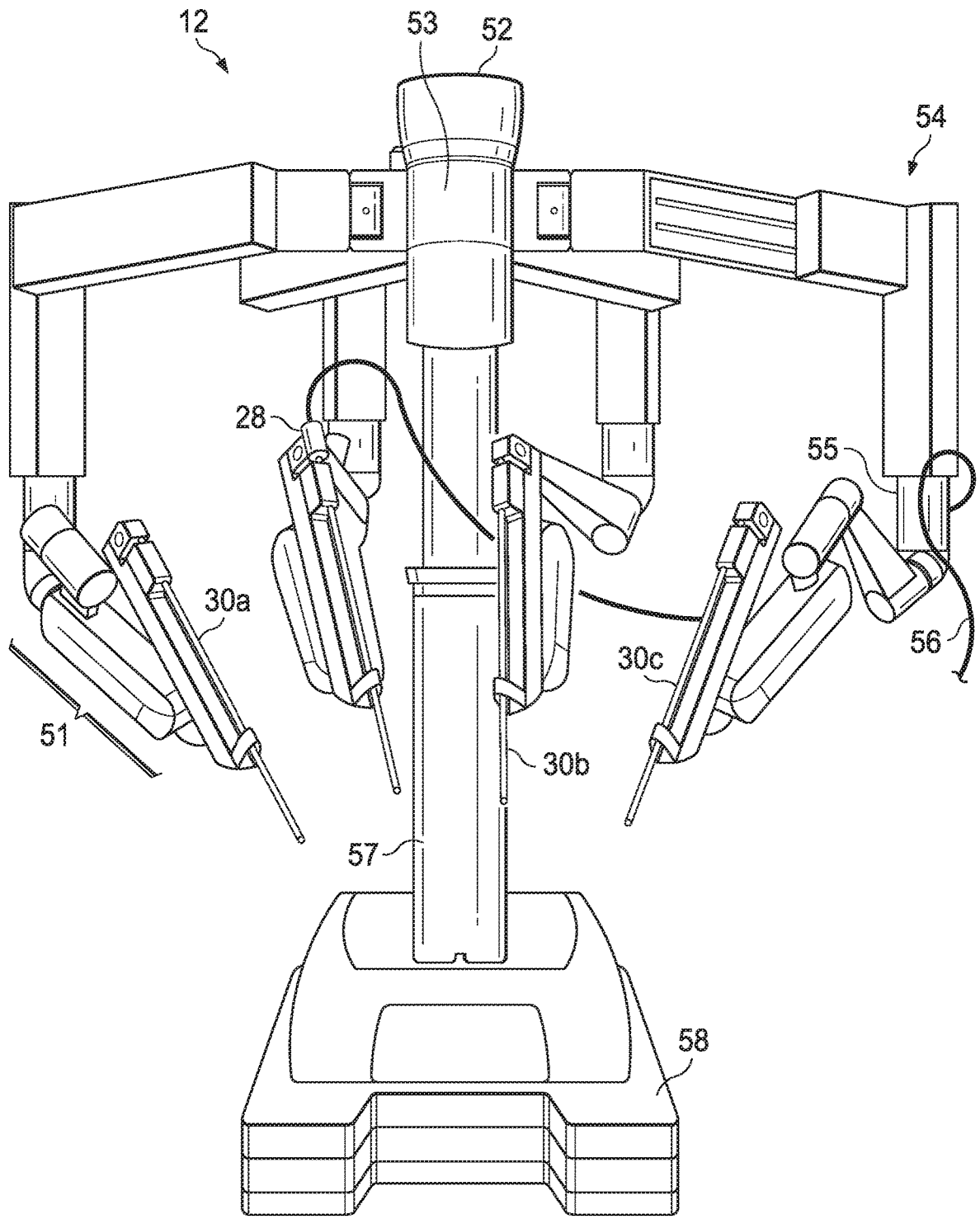
FIG. 1B is a perspective view of a teleoperational manipulator, according to one example of principles described herein.

FIG. 1B is a perspective view of one embodiment of a teleoperational assembly 12 which may be referred to as a patient side cart. The patient side cart 12 shown provides for the manipulation of three surgical tools 30a, 30b, 30c (e.g., instrument systems 14) and an imaging device 28 (e.g., endoscopic imaging system 15), such as a stereoscopic endoscope used for the capture of images of the site of the procedure. The imaging device may transmit signals over a cable 56 to the control system 20. Manipulation is provided by teleoperative mechanisms having a number of joints. The imaging device 28 and the surgical tools 30a-c can be positioned and manipulated through incisions in the patient or through a natural orifice (e.g., oral cavity) so that a kinematic remote center is maintained at the entry to minimize the size of the incision or to avoid damage to the natural orifice boundaries. Images of the surgical environment within the patient anatomy can include images of the distal ends of the surgical tools 30a-c when they are positioned within the field-of-view of the imaging device 28.

The patient side cart 22 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 22 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument 26. The manipulator arms 51 may be teleoperatable. In some examples, the arms 54 connecting to the orienting platform are not teleoperatable. Rather, such arms 54 are positioned as desired before the surgeon 18 begins operation with the teleoperative components.

Endoscopic imaging systems (e.g., systems 15, 28) may be provided in a variety of configurations including rigid or flexible endoscopes. Rigid endoscopes may include a rigid tube, housing a relay lens system, for transmitting an image from a distal end to a proximal end of the endoscope. Flexible endoscopes may transmit images using one or more flexible optical fibers. Digital image based endoscopes have a "chip on the tip" design in which a distal digital sensor such as a one or more charge-coupled device (CCD) or a complementary metal oxide semiconductor (CMOS) device acquire image data and acquired image data can be transferred over a wired or wireless interface. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

Figure 1C:
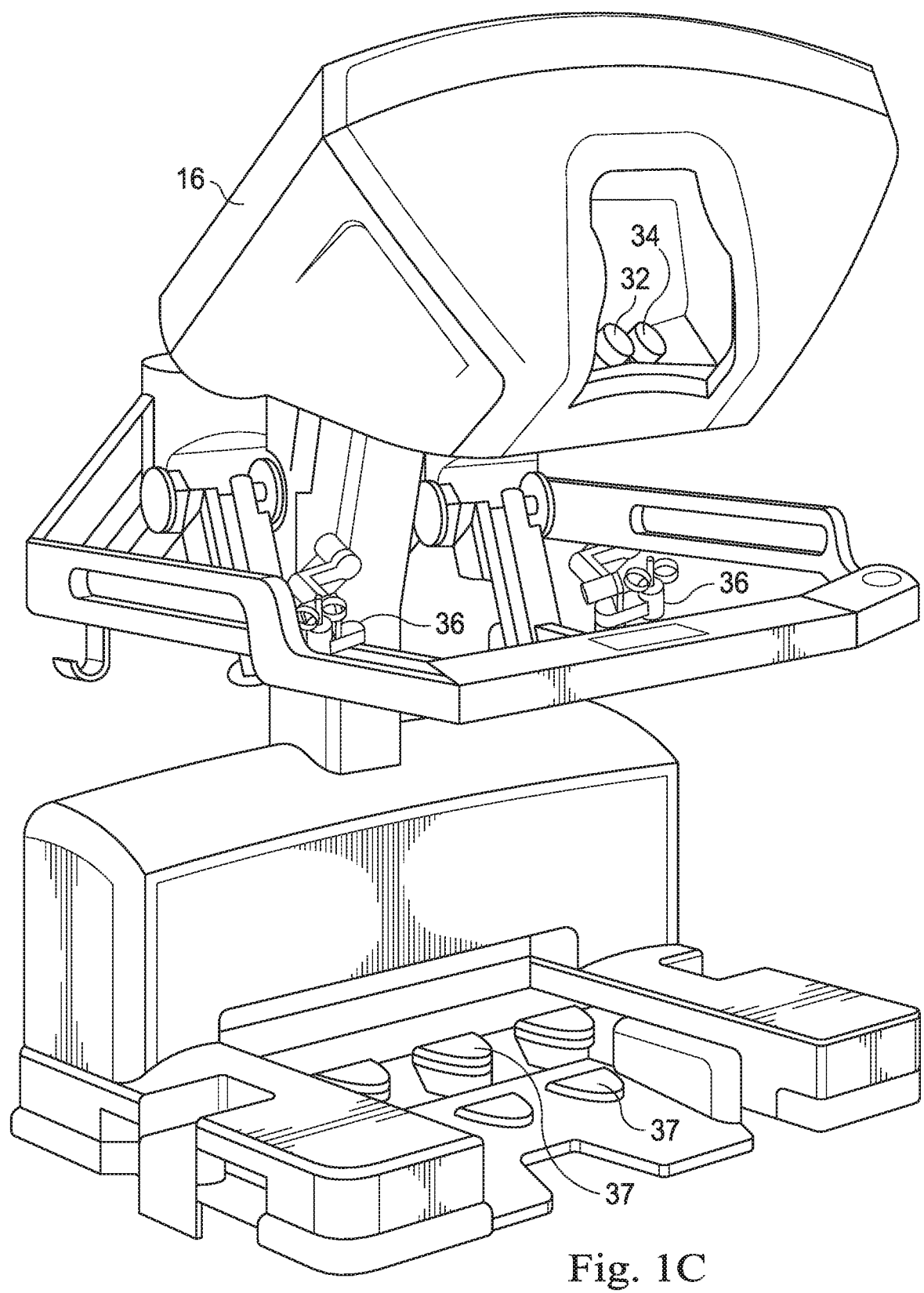
FIG. 1C is a perspective view of a surgeon's control console for a teleoperational medical system, in accordance with many embodiments.

FIG. 1C is a perspective view of the surgeon's console 16. The surgeon's console 16 includes a left eye display 32 and a right eye display 34 for presenting the surgeon S with a coordinated stereo view of the surgical environment that enables depth perception. The displayed image of the surgical environment may be obtained from an imaging system such as the endoscopic imaging system. Additionally or alternatively, the displayed image of the surgical environment may include images from anatomic models created from pre-operative or intra-operative anatomic image datasets. Pre-operative or intraoperative image datasets of the patient anatomy may be obtained using external or non-invasive imaging technology such as computed tomography (CT), single-photon emission CT (SPECT), positron emission tomography (PET), magnetic resonance (MR) imaging, MR thermography, ultrasound, optoacoustic imaging, fluorescence imaging, optical coherence tomography (OCT), confocal endomicroscopy, infrared thermal imaging, impedance imaging, hyperspectral imaging, X-ray fluoroscopy, or the like. Software alone or in combination with manual input is used to convert the recorded images into segmented two dimensional or three dimensional composite models representing a partial or an entire anatomical organ or anatomical region. An anatomic model image dataset is associated with the composite representation. The images used to generate the composite representation may be recorded preoperatively or intra-operatively during a clinical procedure. The pre-operative or intra-operative image data may be presented as two-dimensional, three-dimensional, or four-dimensional (including e.g., time based or velocity based information) images or as images from models created from the pre-operative or intra-operative image data sets. Images from different imaging modalities may be displayed one at a time (e.g., the surgeon may toggle through the different modality images), may be displayed in parallel (e.g., in multiple windows of a composite display) or one may be overlaid or superimposed on the other.

The console 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36. Input control devices 37 are foot pedals that receive input from a user's foot.

During a teleoperational procedure in which the surgical environment within the patient anatomy is viewed from the vantage point of the distal end of the endoscope, the surgeon may have limited awareness of the area beyond the view of the endoscope, both inside the patient anatomy and external of the patient anatomy. The techniques described below provide the surgeon with an expanded situational awareness by merging information from preoperative or intraoperative imaging datasets registered with the endoscopic image dataset. These techniques allow the surgeon to virtually move away from the vantage point of the distal end of the endoscope and view images from the endoscopic image dataset from a different vantage point.

Figure 2:
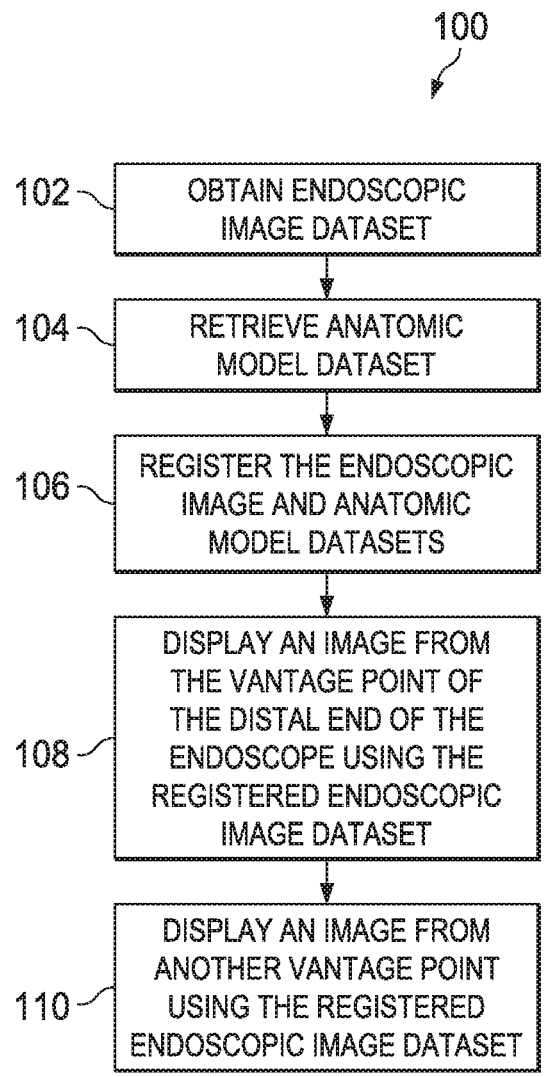
FIG. 2 illustrates a method of displaying an endoscopic image, registered to an anatomic model, from different vantage points.

FIG. 2 is a flowchart illustrating a method 100 of displaying an endoscopic image from different vantage points. The method 100 is illustrated in FIG. 2 as a set of operations or processes. Not all of the illustrated processes may be performed in all embodiments of method 100. Additionally, one or more processes that are not expressly illustrated in FIG. 2 may be included before, after, in between, or as part of the illustrated processes. In some embodiments, one or more of the processes of method 100 may be implemented, at least in part, in the form of executable code stored on non-transitory, tangible, machine-readable media that when run by one or more processors (e.g., the processors of control system 20) may cause the one or more processors to perform one or more of the processes.

At a process 102, an endoscopic image dataset is obtained by an endoscopic system (e.g., system 15, 28) during a medical procedure in a patient anatomy. The endoscopic image dataset may be a two-dimensional image dataset for generation of a single two-dimensional image for presentation on a display of the surgeon's console 16. Alternatively, the endoscopic image dataset may be pair of a two-dimensional image datasets for generation of paired two-dimensional images (one for each eye display 34) for presentation as a stereoscopic image to the surgeon at the surgeon's console 16. Alternatively, the endoscopic image dataset may be a three-dimensional image dataset acquired via a depth camera (also known as ranging camera or RGB-D camera) to be rendered stereoscopically and displayed for presentation as a stereoscopic image to the surgeon at the surgeon's console 16. The stereoscopic image creates the impression of a three-dimensional image using the paired two-dimensional images. The endoscopic image dataset may be a live image dataset from a vantage point of the current location of the distal end of the endoscope or a previously recorded image data set from the vantage points of previous locations of the distal end of the endoscope. The endoscopic image dataset may also be considered to include both the live image data and the previously recorded image data, allowing for replay or reviewing of patient anatomy from selectable, historic vantage points of the distal end of the endoscope.

At a process 104, an anatomic model dataset of the patient anatomy is retrieved from a memory (e.g. memory 24). Pre-operative or intraoperative anatomic model datasets of the patient anatomy may be obtained using external or non-invasive imaging technology such as computed tomography (CT) or magnetic resonance imaging (MRI). The anatomic model datasets are stored for later retrieval. In this example, an image dataset is associated with a composite model representation of a partial or an entire anatomical organ or anatomical region.

At a process 106, the endoscopic image dataset is registered to the anatomic model dataset. Various registration techniques have been described, for example, U.S. patent application Ser. No. 14/862,692, filed Sep. 23, 2015, disclosing "Collision Avoidance During Controlled Movement of Image Capturing Device and Manipulatable Device Movable Arms;" U.S. patent application Ser. No. 14/916,854, filed Mar. 4, 2016, disclosing "Shape Sensor Systems For Localizing Movable Targets;" U.S. patent application Ser. No. 15/126,480, filed Sep. 15, 2016, disclosing "Methods and Devices for Tele-Surgical Table Registration;" U.S. Provisional Patent Application No. 62/443,460, filed Jan. 6, 2017, disclosing "Registration and Coordinated Manipulation of Augmented Reality Image Component;" and U.S. Provisional Patent Application No. 62/112,416, filed Feb. 5, 2015, disclosing "System and Method For Anatomical Markers," which are incorporated by reference herein their entirety. Registering the endoscopic image dataset with the anatomic model dataset allows the two dimensional stereoscopic endoscope image data to be projected or mapped onto a three-dimensional volume in space defined by the anatomic model. In one embodiment, a two dimensional pixel or point cloud generated from the endoscopic image dataset is projected on to the three-dimensional volume defined by the anatomic model. Alternative methods for mapping two-dimensional image datasets to three-dimensional volumes may also be used. For example, a two dimensional pixel or point cloud generated from the endoscopic image dataset may be three-dimensionally mapped based on depth sensor or other point depth mapping data. The registered endoscopic image dataset is a three-dimensionally mapped dataset.

Figure 3:
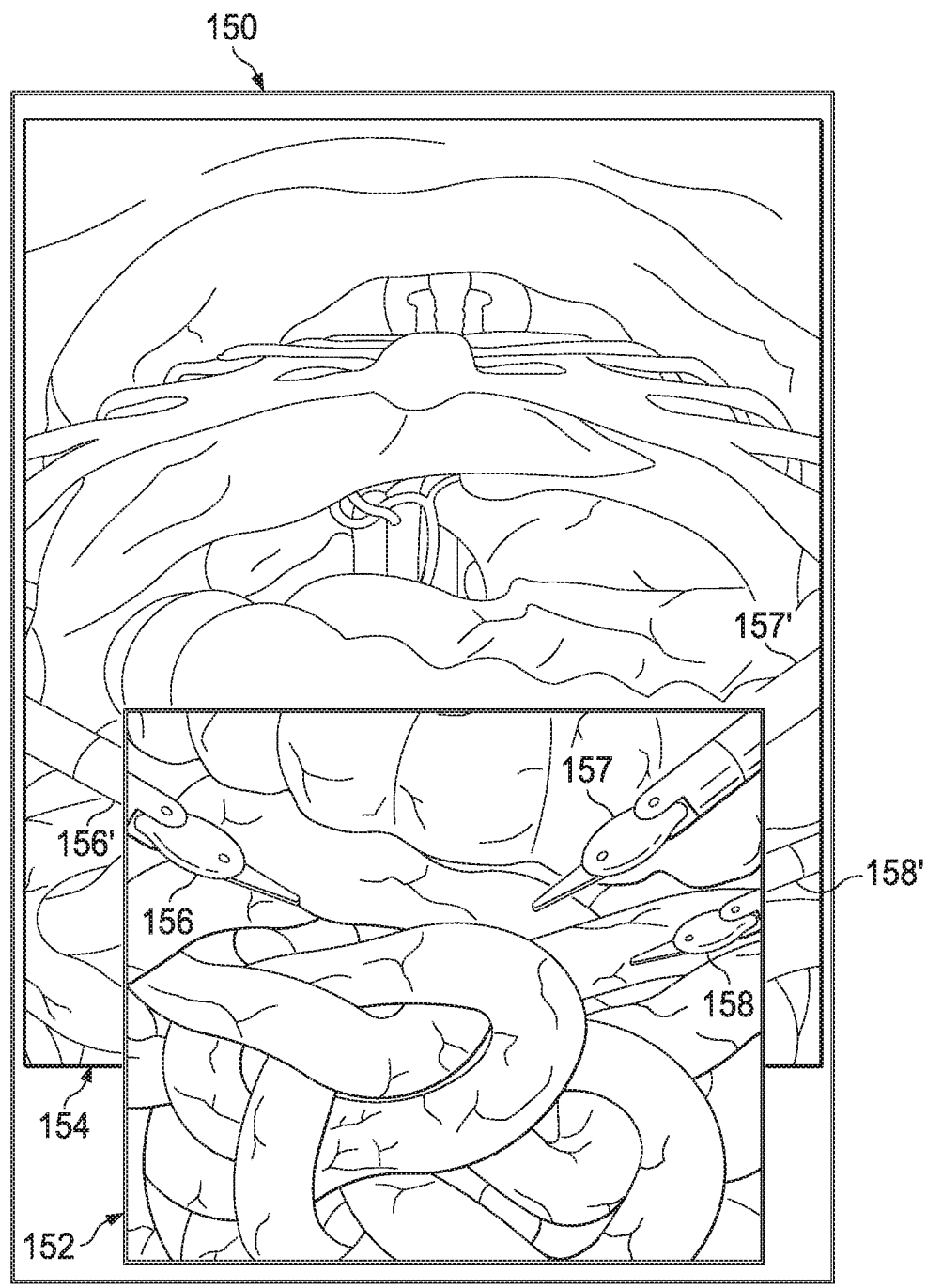
FIG. 3 is a display of a surgical environment including an endoscopic image overlaid on an anatomic model image.

At a process 108, the three-dimensionally mapped endoscopic image dataset is used to generate and display an image from a vantage point that may assist the surgeon. For example, an initial vantage point may be the viewpoint from the distal end of the endoscope within the patient anatomy (i.e., the conventional endoscopic view from the endoscope). The initial vantage point image may be constructed based on the three dimensional point cloud. FIG. 3 illustrates a display 150 visible by a surgeon at the operator console or on another display screen. The display 150 includes an endoscopic image 152 of a surgical environment including instruments 156, 157, 158. The image 152 is generated from the mapped endoscopic image dataset. Optionally, the display 150 includes an anatomic model image 154 generated from the anatomic model dataset. In this example, the endoscopic image 152 is overlaid, superimposed, blended or otherwise mapped onto the anatomic model image 154. The display 150 also includes instrument illustrations 156', 157', 158' overlaid or superimposed on the anatomic model image 154. The instrument illustrations 156', 157', 158' may be generated based on instrument pose and relative scale, known or determined from kinematic chain, position or shape sensor information, vision-based tracking or a combination of those. Various tool tracking techniques have been described, for example in U.S. patent application Ser. No. 11/865,014, filed Sep. 30, 2007, disclosing "METHODS AND SYSTEMS FOR ROBOTIC INSTRUMENT TOOL TRACKING WITH ADAPTIVE FUSION OF KINEMATICS INFORMATION AND IMAGE INFORMATION" and U.S. patent application Ser. No. 11/130,471, filed May 16, 2005. disclosing "Methods and system for performing 3-D tool tracking by fusion of sensor and/or camera derived data during minimally invasive robotic surgery," which are incorporated by reference herein their entirety. The display 150 thus provides the surgeon with additional environmental context beyond that provided by the endoscopic image 152 alone. For example, the anatomic model image 154 illustrates additional organs, bones, and tumors not visible on the endoscopic image 152, and the instrument illustrations 156', 157', 158' provide information about instrument trajectories not visible on the endoscopic image. In some embodiments, the endoscopic image 152 may be distinguishable from the anatomic model image 154 by a border illustration, color differences (e.g., the endoscopic image in color, and the anatomic model image in grayscale), in brightness, or other distinguishing characteristics.

In various embodiments, the overlaid endoscopic image may have differing levels of transparency. For example, the overlaid endoscopic image may allow the anatomic model image to be visible through the endoscopic image. The level of transparency may be adjusted by the user, may be adjusted based on the content of the scene anatomical models (i.e. to make critical structures or target lesions to stand out in the image) or may be adjusted based on obstructions (e.g., blood, debris) in the endoscopic view.

Figure 4:
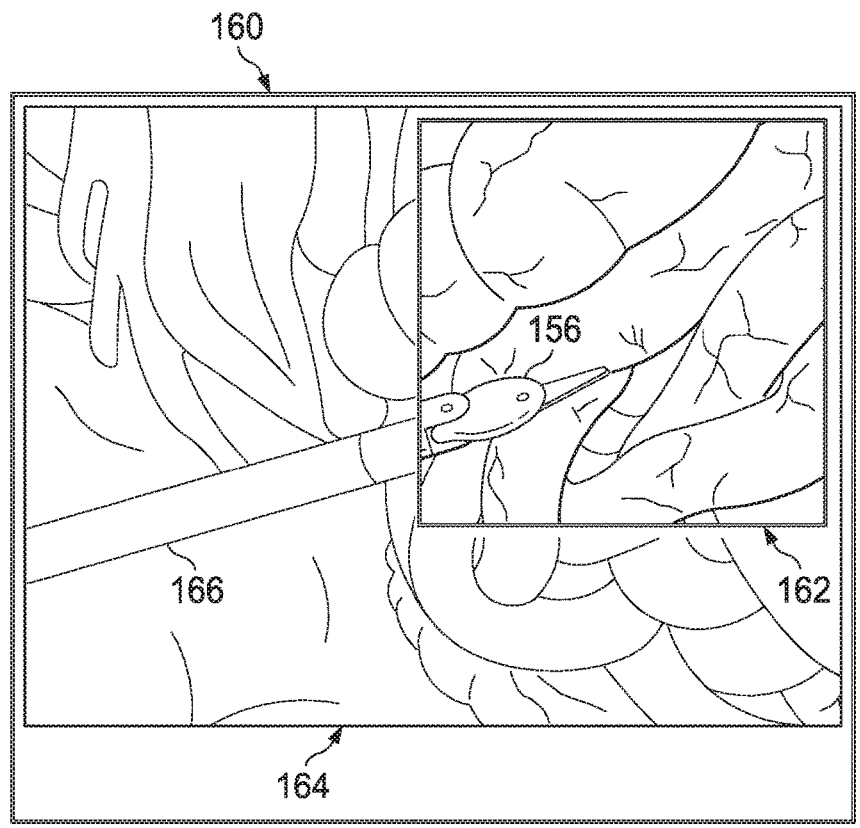
FIG. 4 is a display of the surgical environment of FIG. 3 from a different vantage point, including an endoscopic image overlaid on an anatomic model image.

Referring again to FIG. 2, at a process 110, the three-dimensionally mapped endoscopic image dataset is used to generate and display an image from a different vantage point that may assist the surgeon. The surgeon may select the other vantage point from a plurality of optional vantage points or may virtually rotate or otherwise move away from the initial vantage point to visualize the three-dimensionally mapped endoscopic image dataset from a different perspective such as a perspective orthogonal to or oblique from the initial vantage point. When viewing the endoscopic image dataset from the second vantage point some anatomic structures and/or instruments (i.e., the pixels forming the image of the anatomic structures and/or instruments) may no longer be visible. FIG. 4 illustrates a display 160 of the surgical environment of FIG. 3 from a second vantage point, generally lateral of the initial vantage point. The display 160 includes an endoscopic image 162 of the surgical environment from the second vantage point. The image 162 is generated from the same mapped endoscopic image dataset used to generate image 152 from the initial vantage point. Because the image dataset has been three dimensionally mapped, images may be generated from multiple perspectives or vantage points, in addition to the original vantage point at the end of the endoscope. From the second vantage point, the endoscopic image 162, allows the surgeon to view the instrument 156 and the surrounding tissue more closely. The endoscopic image from the second vantage point does not include the instruments 157, 158 because they are not visible from the second vantage point, due to intervening tissue. In other words, a sub-portion of the pixel cloud used to generate the endoscopic image 152 may be used to generate the image 162.

Optionally, the display 160 includes an anatomic model image 164 generated from the anatomic model dataset. In this example, the endoscopic image 162 is overlaid, superimposed, blended or otherwise mapped onto the anatomic model image 164. The display 160 also includes an instrument illustration 166 overlaid or superimposed on the anatomic model image 164. The instrument illustration 166 may be generated based on instrument pose and scaling known or determined from kinematic chain, position or shape sensor information, vision-based tracking or a combination of those. The display 160 thus provides the surgeon with additional environmental context beyond that provided by the endoscopic image 162 alone. For example, the anatomic model image 164 illustrates additional organs and bones not visible on the endoscopic image 162, and the instrument illustration 166 provides information about instrument trajectories not visible on the endoscopic image. From the second vantage point, the surgeon is able to observe a more expansive anatomical area while still maintaining awareness of the direct view from the endoscope. The display of the anatomic model image 164 is optional because in some examples, the endoscopic image 162 alone, presenting the three-dimensionally mapped endoscopic image dataset from the second vantage point, may provide the surgeon with sufficient spatial perspective.

Figure 5:
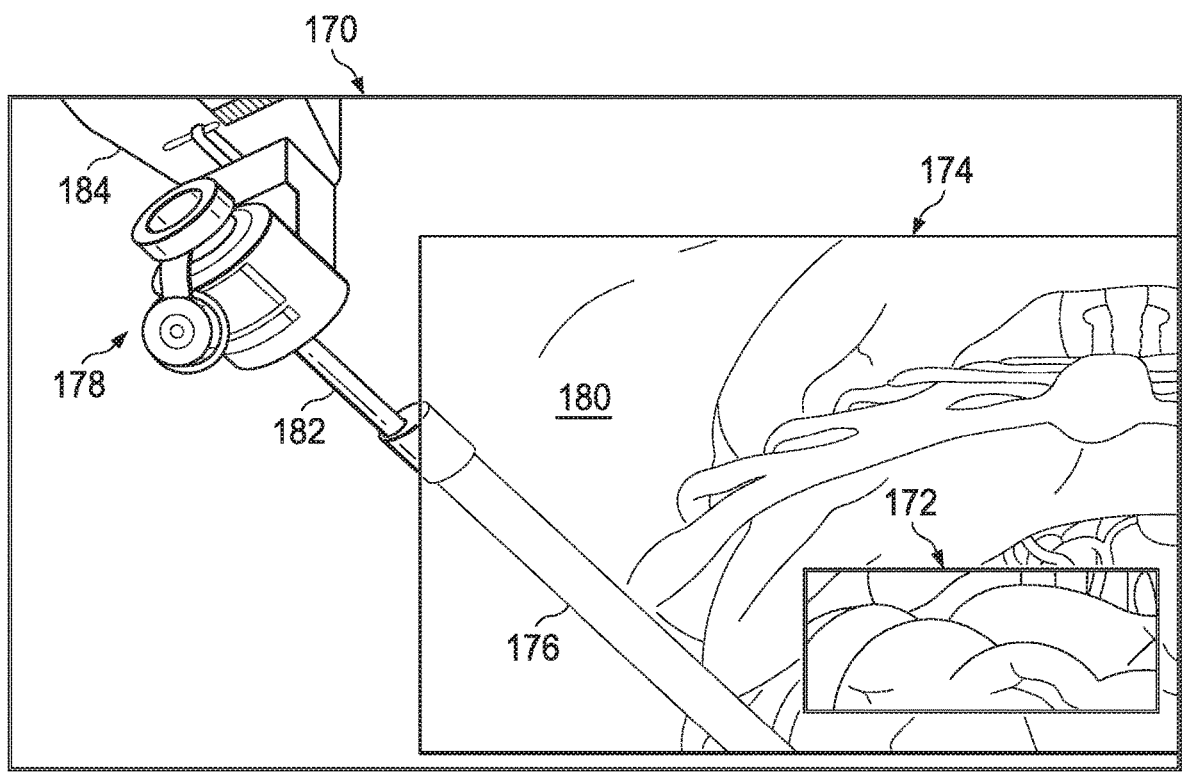
FIG. 5 is a display of the surgical environment of FIG. 3 from a different vantage point and including the environment external to the patient anatomy.

FIG. 5 illustrates a display 170 of the surgical environment of FIG. 3 from a third vantage point. In this example, the surgical environment external to the patient anatomy is also illustrated. The display 170 includes an endoscopic image 172 of the surgical environment from a third vantage point. The image 172 is generated from the same mapped endoscopic image dataset used to generate images 152, 162. Because the image dataset has been three dimensionally mapped, images may be generated from multiple perspectives or vantage points, in addition to the original vantage point at the end of the endoscope. From the third vantage point, the endoscopic image 172 itself provides the surgeon with relatively little content but is useful in helping the surgeon maintain awareness of the endoscopic view with respect to the greater surgical environment.

Optionally, the display 170 includes an anatomic model image 174 generated from the anatomic model dataset. In this example, the endoscopic image 172 is overlaid, superimposed, blended or otherwise mapped onto the anatomic model image 174. The display 170 also includes an illustration 176 of the instrument 156 overlaid or superimposed on the anatomic model image 174. The illustrated instrument 176 may be generated based on pose and/or poses of instrument 156 known or determined from kinematic chain, position or shape sensor information, vision-based tracking or a combination of those. The display 170 thus provides the surgeon with additional environmental context beyond that provided by the endoscopic image 172 alone. For example, the anatomic model image 174 illustrates additional organs and bones not visible on the endoscopic image 172, and the instrument illustration 176 provides information about instrument trajectories not visible on the endoscopic image. Optionally, the display 170 includes an illustration 178 of the surgical environment external of the patient anatomy. In this example, display 170 includes the instrument illustration 176 which shows the instrument extending through an image of the patient's anatomic wall 180. The image of the patient's anatomic wall may be part of the anatomic model image 174. External to the patient's anatomic wall 174 in the external environment illustration 178 is an illustration 182 of the proximal end of the instrument 156 extending outside of the patient anatomy. The proximal end of the instrument 156 is coupled to a teleoperational manipulator arm 184 (e.g., manipulator arm 51). The external environment illustration 178 may be generated based on instrument and manipulator arm positions known or determined from kinematic chain, position or shape sensor information, visual tracking based on a camera external to the patient anatomy or a combination of those. For example, with the teleoperational manipulator, the patient, the endoscopic system, and the anatomic model all registered to a common surgical coordinate system, a composite virtual image of the surgical environment beyond the vantage point endoscopic image can be generated based on the anatomic model dataset and known kinematic and/or structural relationships of the components of the teleoperational system. The display 170 thus provides the surgeon with additional environmental context beyond that provided by the endoscopic image 172 alone. From the third vantage point of FIG. 5, the surgeon is able to observe a more expansive intra- and extra-anatomical area while still maintaining awareness of the view from the distal end of the endoscope.

Figure 6:
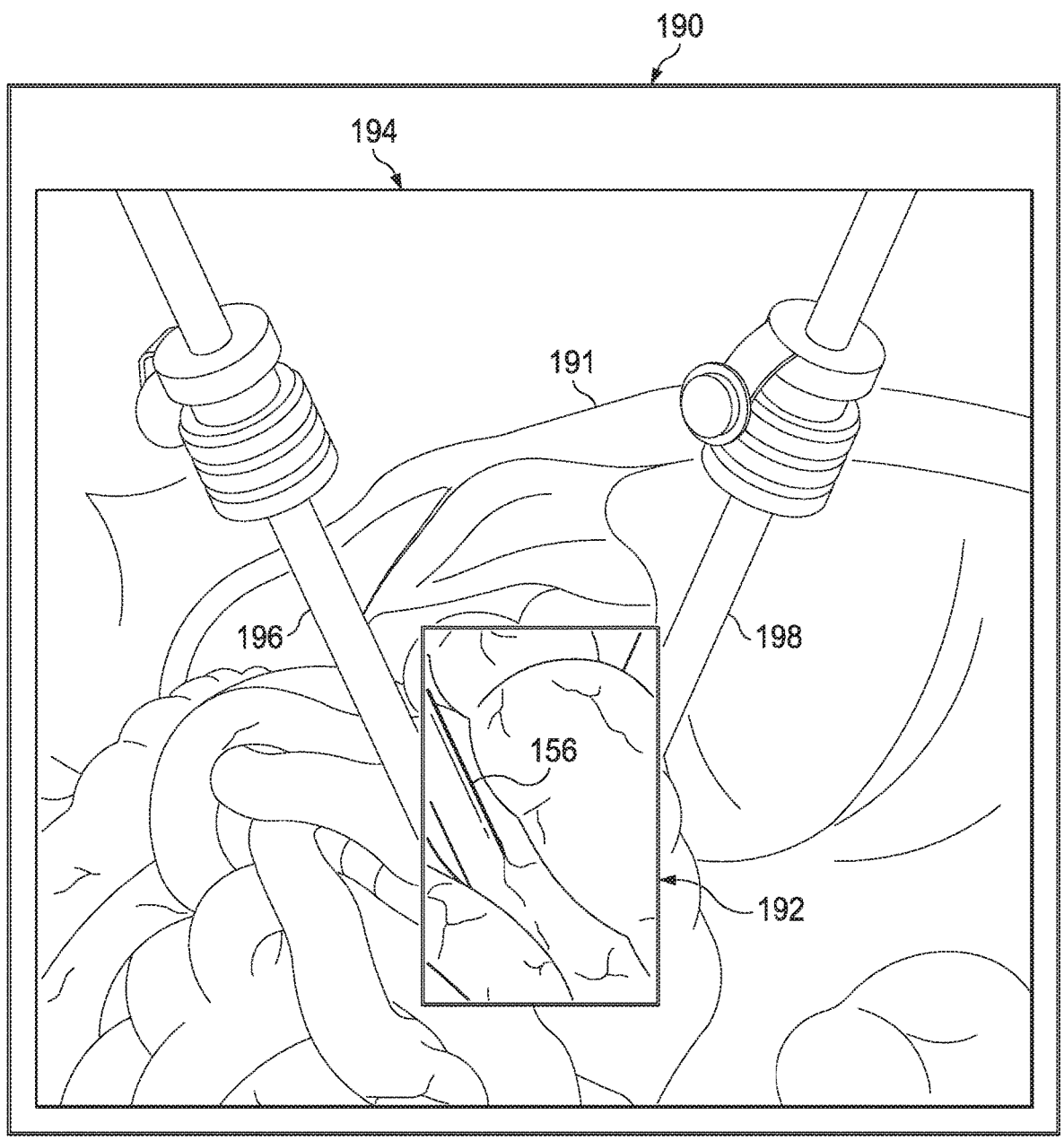
FIG. 6 is a display of the surgical environment of FIG. 3 from a different vantage point external to the patient anatomy.

FIG. 6 is a display 190 of the surgical environment of FIG. 3 from a fourth vantage point, external to the patient anatomy. In this example, cross-sectional portions of the patient anatomy, including the anatomic wall 180, are illustrated. The display 190 includes an endoscopic image 192 of the surgical environment from the fourth vantage point. The image 192 is generated from the same mapped endoscopic image dataset used to generate images 152, 162, 172. Because the image dataset has been three dimensionally mapped, images may be generated from multiple perspectives or vantage points, in addition to the original vantage point at the end of the endoscope. From the fourth vantage point, the endoscopic image 192 provides the surgeon with a contextual image that allows the surgeon to understand the relationship between the endoscope view and the broader surgical environment.

Optionally, the display 190 includes an anatomic model image 194 generated from the anatomic model dataset. In this example, the endoscopic image 192 is overlaid, superimposed, blended or otherwise mapped onto the anatomic model image 194. The display 190 also includes an illustration 196 of the instrument 156 and an illustration 198 of the endoscopic instrument (e.g. endoscope 15, 28) overlaid or superimposed on the anatomic model image 194. The illustrated instruments 196, 198 may be generated based on positions and/or poses of the instruments known or determined from kinematic chain and/or position sensor information. The display 190 thus provides the surgeon with additional environmental context beyond that provided by the endoscopic image 192 alone. For example, the anatomic model image 194 illustrates surface or cut-away views of additional organs and bones not visible on the endoscopic image 192, and the instrument illustrations 196, 198 provide information about instrument trajectories not visible on the endoscopic image. For example, from the display 190, the surgeon can have a better contextual understanding of the location of the distal end of the endoscopic instrument and the area surrounding the endoscopic image 192 taken from the vantage point of the distal end of the endoscopic instrument. The display 190 thus provides the surgeon with additional environmental context beyond that provided by the endoscopic image 192 alone. From the fourth vantage point of FIG. 6, the surgeon is able to observe a more expansive intra- and extra-anatomical area while still maintaining awareness of the view from the distal end of the endoscope.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
   a teleoperational assembly including a plurality of manipulators, wherein a first manipulator of the plurality of manipulators is configured to control movement of an endoscopic imaging system; and a processing unit including one or more processors, wherein the processing unit is configured to:
  obtain an endoscopic image dataset of a patient anatomy from the endoscopic imaging system;
  retrieve an anatomic model dataset of the patient anatomy obtained by an anatomic imaging system;
  map the endoscopic image dataset onto a three-dimensional volume defined by the anatomic model dataset;
  display a first vantage point image using the mapped endoscopic image dataset, the first vantage point image presented from a first vantage point at a distal end of the endoscopic imaging system; and
  display a second vantage point image using at least a portion of the mapped endoscopic image dataset, the second vantage point image presented from a second vantage point, different from the first vantage point.

2. The system of claim 1 wherein the first and second vantage points are inside the patient anatomy.

3. The system of claim 1 wherein the second vantage point is outside of the patient anatomy.

4. The system of claim 1 wherein mapping the endoscopic image dataset to the anatomic model dataset includes mapping a two dimensional point cloud from the endoscopic image dataset into a three dimensional point cloud based on the anatomic model dataset.

5. The system of claim 4 wherein displaying the first vantage point image includes constructing the first vantage point image from the three dimensional point cloud.

6. The system of claim 1 wherein the processing unit is further configured to:
  display a first three-dimensional anatomic model image generated from the anatomic model dataset, with the first vantage point image.

7. The system of claim 6 wherein the processing unit is further configured to:
  display a second three-dimensional anatomic model image generated from the anatomic model dataset, with the second vantage point image.

8. The system of claim 6 wherein displaying the first three-dimensional anatomic model image with the first vantage point image includes projecting the first vantage point image onto the first three-dimensional anatomic model image.

9. The system of claim 8 wherein the processing unit is further configured to:
  display a second three-dimensional anatomic model image, generated from the anatomic model dataset, with the second vantage point image.

10. The system of claim 6 wherein displaying the first three-dimensional anatomic model image with the first vantage point image includes depth matching the endoscopic image dataset to the anatomic model dataset.

11. The system of claim 6 wherein displaying the first three-dimensional anatomic model image with the first vantage point image includes scaling the first three-dimensional anatomic model image to the first vantage point image.

12. The system of claim 1 wherein the endoscopic image dataset includes a first two dimensional image dataset and the anatomic model dataset includes a three-dimensional anatomic model dataset, wherein mapping includes mapping the first two dimensional image dataset to the three-dimensional anatomic model dataset.

13. The system of claim 12 wherein the endoscopic image dataset includes a second two dimensional image dataset such that the first and second two dimensional image datasets form a stereoscopic image dataset, wherein mapping includes mapping the second two dimensional image dataset to the three-dimensional anatomic model dataset.

14. The system of claim 1 wherein the anatomic imaging system is a computed tomography imaging system.

15. The system of claim 1 wherein the second vantage point image is from a recorded image from a previous vantage point of the distal end of the endoscopic imaging system.

16. The system of claim 1 wherein the processing unit is further configured to:
  track a medical instrument positioned within the patient anatomy, the medical instrument coupled to a second manipulator of the plurality of manipulators; and
  display a simulated image of the tracked medical instrument extending from the patient anatomy with the displayed second vantage point image.

17. The system of claim 16, wherein the simulated image of the tracked medical instrument is generated based on a position of the medical instrument generated from shape sensor information.

18. The system of claim 16, wherein the simulated image of the tracked medical instrument is generated based on a position of the medical instrument generated from kinematic chain information.

19. The system of claim 16, wherein the simulated image of the tracked medical instrument is generated based on a position of the medical instrument generated from a camera using vision-based tracking.

20. The system of claim 1, wherein the endoscopic image dataset comprises live image data and recorded image data.

* * * * *